United States Patent [19]
Richardson et al.

[11] Patent Number: 5,325,897
[45] Date of Patent: Jul. 5, 1994

[54] FLUID CATCH COLLECTOR FOR SAMPLING AND DRAIN VALVES

[76] Inventors: Thomas R. Richardson, Rte. 5, Box 6, CR 243; Chris Caso, 521 Holly St., both of Angleton, Tex. 77515

[21] Appl. No.: 45,704

[22] Filed: Apr. 14, 1993

[51] Int. Cl.⁵ ............................................. G01N 1/10
[52] U.S. Cl. .................................... 141/86; 141/88; 141/97; 141/130; 141/98; 222/108; 73/863.81; 73/863.86
[58] Field of Search ...................... 141/130, 86, 87, 88, 141/98, 311 A, 392, 97; 222/108; 137/312, 313; 422/100, 99; 73/863.81, 863.86

[56] References Cited

U.S. PATENT DOCUMENTS

| | | | |
|---|---|---|---|
| 3,933,186 | 1/1976 | Scheffler | 141/97 |
| 4,454,943 | 6/1984 | Moller | 73/863.86 X |
| 4,479,393 | 10/1984 | Shores | 73/863.86 X |
| 4,524,811 | 6/1985 | Taylor | 141/325 |
| 4,583,572 | 4/1986 | Morris | 141/97 |
| 4,651,574 | 3/1987 | Spencer | 73/863.86 |
| 4,899,601 | 2/1990 | Lee | 73/864.63 |
| 4,925,627 | 5/1990 | Johnson | 422/99 |
| 4,989,463 | 2/1991 | Cimaglia et al. | 73/863.86 |
| 5,029,484 | 7/1991 | Somers et al. | 73/863.81 |
| 5,063,977 | 11/1991 | Belland | 141/86 |
| 5,099,872 | 3/1992 | Tarvin et al. | 141/88 UX |
| 5,165,574 | 11/1992 | Ratcliffe | 222/108 |
| 5,189,919 | 3/1993 | Hernandez | 73/863.43 |

FOREIGN PATENT DOCUMENTS

| | | | |
|---|---|---|---|
| 0237342 | 11/1985 | Japan | 73/863.81 |
| 2107282 | 4/1983 | United Kingdom | 73/863.86 |

*Primary Examiner*—Ernest G. Cusick
*Attorney, Agent, or Firm*—Richard C. Litman

[57] ABSTRACT

A fluid catch container for sampling and drain valves provides for the containment of any residue which may leak or drip from the outlet of such a valve. The container is selectively openable and closable, providing easy access for the taking of a sample or for the draining of fluid from the outlet. A rotatable closure serves to prevent the flooding of the catch container due to rain or other agent(s) and the undesirable distribution of any residue due to wind action. The base of the container is removable for emptying and cleaning, and alternatively may be replaced with a fitting for a larger residue collection container. The device is preferably formed of corrosion resistant materials, such as stainless steel, although other materials (e.g., plastics, etc.) may be used. The device is particularly useful in the petroleum, petrochemical, and chemical industries, or any environment where fluid samples must be taken on a regular basis from regular points in a processing system.

14 Claims, 4 Drawing Sheets

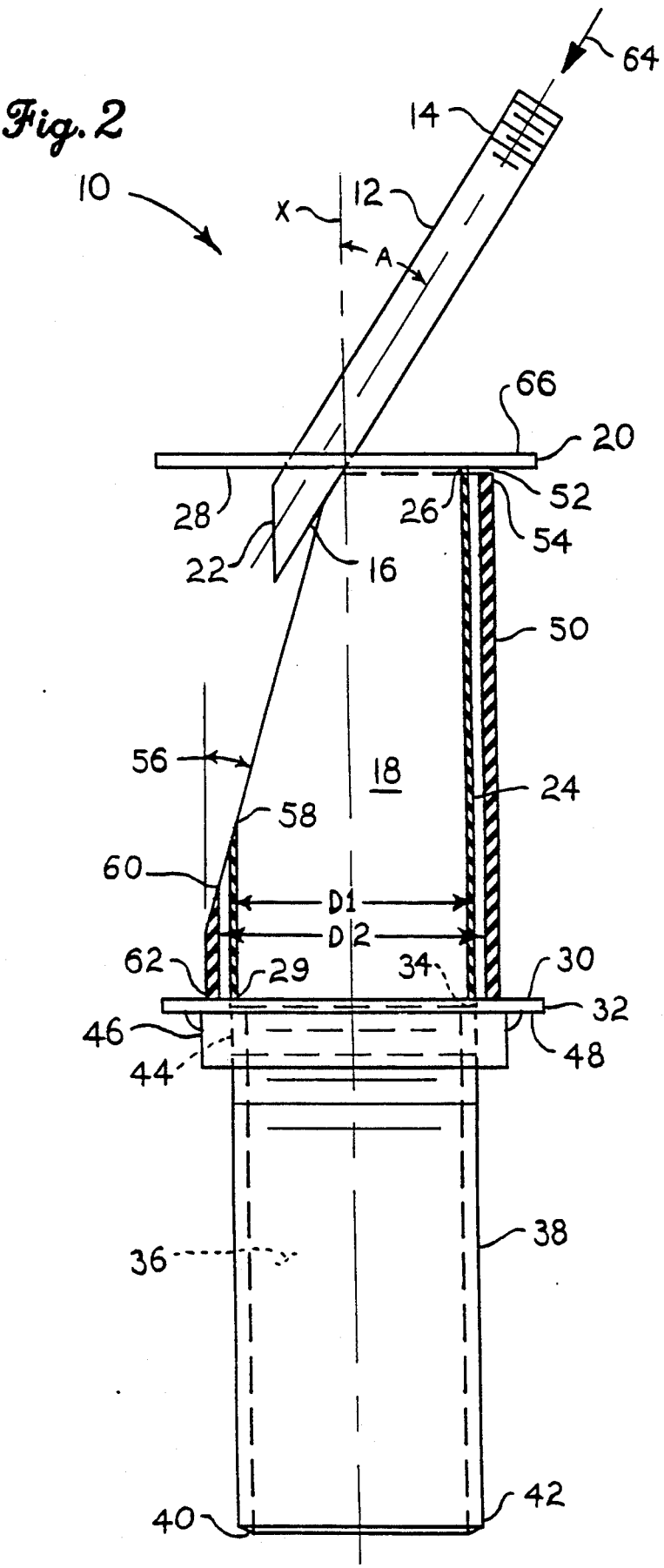

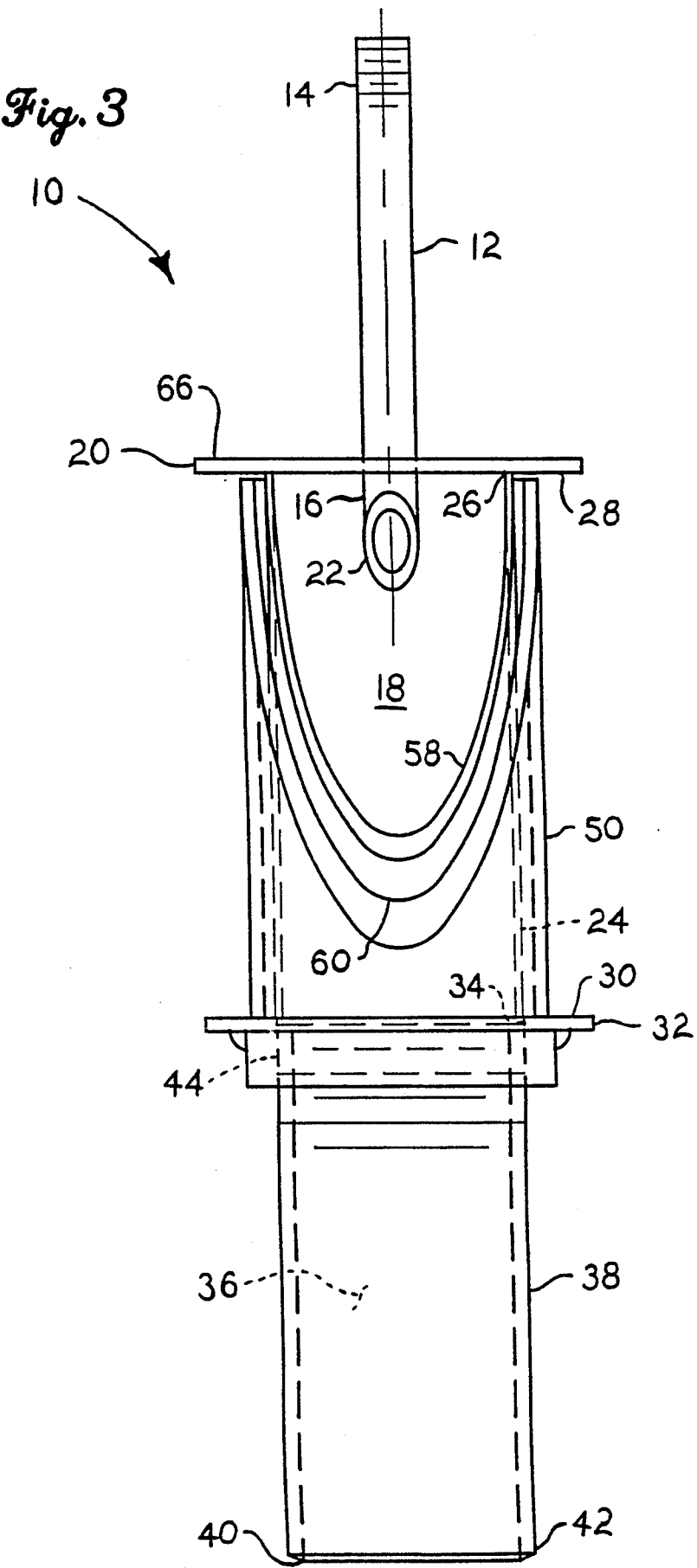

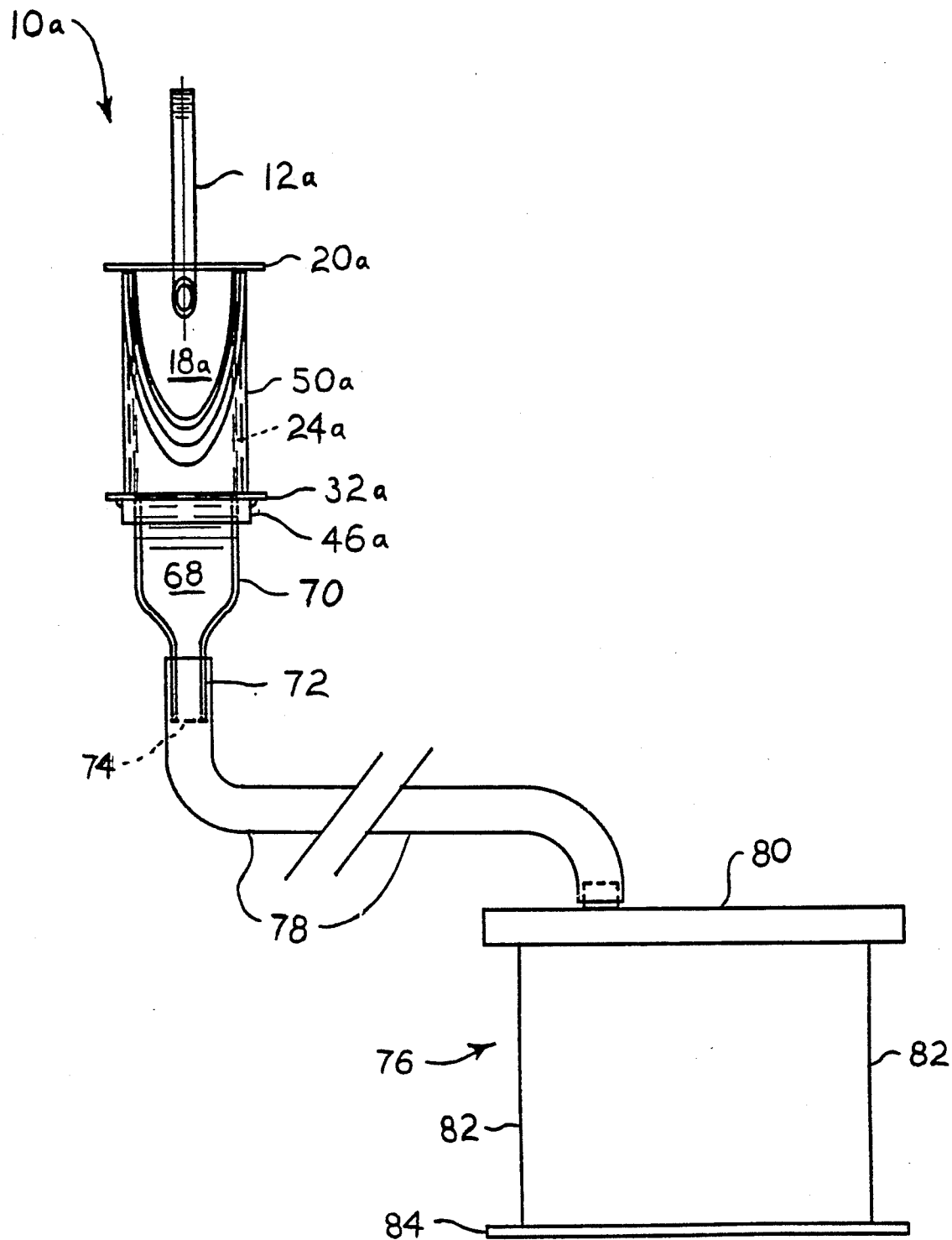

FLUID CATCH COLLECTOR FOR SAMPLING AND DRAIN VALVES

FIELD OF THE INVENTION

The present invention relates generally to containers and receptacles, and more specifically to a closable fluid catch collector or container for use with sampling and drain valves, providing for the containment of excess residue from such valves after the draining or sampling of the fluid therein.

BACKGROUND OF THE INVENTION

It is generally considered standard procedure, if not a requirement, in many industries to take samples of various fluids periodically. In fact, in many industries these samples are taken at regular times and at regular points in the industrial process. The process may be adjusted according to the results obtained from analysis of the sample(s) and depending upon the specific industrial process. The above procedure is generally used in the petroleum, petrochemical, and chemical fields, and is also used in the food processing and other industries. Moreover, from time to time it is necessary to drain a valve, line or tank associated with some part of the system or process in a given industry.

It will be evident that some fluid residue will remain within the pipe or tube downstream from the valve, due to the viscosity and surface tension of the fluid, after a sample is taken or a valve, line or tank is drained. This residue eventually drips from the lower end of the drain or sampling outlet to contaminate the area immediately therebeneath. In many instances, the fluid or chemical residues may be corrosive, poisonous, or otherwise harmful or hazardous. Even in the food industry, such residue may be attractive to vermin or subject to spoilage or otherwise contribute to an unsanitary condition.

Accordingly, the Environmental Protection Agency has formulated regulations requiring that such residues be contained rather than merely allowed to flow outward into the immediate environment. The solution often used is merely to place a bucket, can or other open container immediately below the outlet to catch any residue which may drip therefrom. However, this can be an unsatisfactory solution, particularly for the outdoor environment where the outlet and container are exposed to the weather. In such situations, wind can often blow the dripping residue away from the container below and contaminate the immediate area. Further, rain can easily fill such an open container and cause any residue therein to overflow the container if the residue is less dense than water; a relatively small amount of precipitation may be sufficient to cause such a problem, if the container is positioned so as to catch some amount of runoff from a tank, pipe or valve above.

Another solution is to install a cap on the end of the drain or sample tube or pipe outlet. However, when the cap is removed the residue may overflow the relatively small volume of the cap and contaminate the hand and/or equipment of the worker, thus requiring additional cleanup time and effort, as well as possibly exposing the worker to potential health hazards. As can be seen, none of the solutions developed for the above problem have proven completely satisfactory.

Accordingly, the need arises for a fluid catch collector or container installable on a sampling or drain tube or pipe outlet, which container may be opened temporarily in order to obtain a sample of fluid from the tube or pipe. The container must be closable, in order to preclude the spillage of fluid therein due to wind or other causes and further to prevent the entry of other matter (e.g., rain) into the container. The fluid catch container must also provide means for the draining or removal of fluid residue captured therein, and provide for easy cleanup of the residue container. The device moreover must be adaptable to larger containers as needed.

DESCRIPTION OF THE PRIOR ART

U.S. Pat. No. 4,651,574 issued to R. Wilson Spencer on Mar. 24, 1987 discloses a Sample Injection Means having a specialized valve and container. The device is intended strictly for obtaining a sample, and while a shroud may be secured to the valve, the lower end of the shroud must be removed each time a sample is taken, thereby resulting in the potential of residue dripping from the valve and out the bottom of the open shroud until the lower cap is reinstalled.

U.S. Pat. No. 4,899,601 issued to Sun Y. Lee on Feb. 13, 1990 discloses a Sample Collector wherein the collecting container allows any residue from the sample outlet to drip to the immediate environment when the container is removed. No means is provided for the containment of any residue when the sample collecting container is removed.

U.S. Pat. No. 4,925,627 issued to Gerald K. Johnson on May 15, 1990 discloses an Oil Sampling Device which operates to withdraw oil upward through a dipstick tube. No means is provided for the closure of the sampling outlet, as the dipstick tube serving as the outlet is oriented upward to preclude residue flowing outward therefrom.

U.S. Pat. No. 4,989,463 issued to Karen A. Cimagila et al. on Feb. 5, 1991 discloses a Sample Collection Shield having three closed sides and an open side. No means is disclosed for closing the permanently open side.

U.S. Pat. No. 5,029,484 issued to Scott R. Somers et al. on Jul. 9, 1991 discloses a Hazardous Waste Sampler for the withdrawal of a sample from the top of a drum or the like. The device is more closely related to the Johnson Oil Sampling Device discussed above than to the present invention, in that residue is not likely to flow upward through the sampling outlet after the device is used and accordingly no means to prevent such occurrence is provided.

U.S. Pat. No. 5,165,574 issued to Ralph D. Ratcliffe on Nov. 24, 1992 discloses a Drip Bucket having clamping means to secure to a downwardly oriented outlet. The device is permanently open at the top, thereby potentially allowing rainwater or other agents to flow down the outside of the outlet pipe and into the container to cause it to overflow.

Finally, U.S. Pat. No. 5,189,919 issued to Raymond Hernandez on Mar. 2, 1993 discloses a Wellhead Fluid Sampler. While the disclosure describes the device as being essentially closed, this is not an accurate description as one side is permanently open with no means disclosed providing for its closure, as in the case of the present invention.

None of the above noted patents, taken either singly or in combination, are seen to disclose the specific arrangement of concepts disclosed by the present invention.

SUMMARY OF THE INVENTION

By the present invention, an improved fluid catch collector or container for sampling and drain valves is disclosed.

Accordingly, one of the objects of the present invention is to provide an improved fluid catch collector or container which may be permanently secured to the sampling or drain tube or pipe outlet.

Another of the objects of the present invention is to provide an improved fluid catch collector or container which may be essentially closed when no sample is being taken or drained, thereby precluding any flooding or windblown transmission of any residue contained therein and further preventing the contamination of the interior of the drain tube or pipe by windblown or other matter.

Yet another of the objects of the present invention is to provide an improved fluid catch collector or container which is easily openable and accessible for the collection of a sample of fluid or the draining of the outlet therein.

Still another of the objects of the present invention is to provide an improved fluid catch collector or container which provides for the removal of a collection container for the emptying and cleaning thereof.

A further object of the present invention is to provide an improved fluid catch collector or container which is resistant to attack from various hazardous, corrosive or other chemicals.

An additional object of the present invention is to provide an improved fluid catch collector or container which optionally provides for a greater volume of fluid residue storage.

A final object of the present invention is to provide an improved fluid catch collector or container for the purposes described which is inexpensive, dependable and fully effective in accomplishing its intended purpose.

With these and other objects in view which will more readily appear as the nature of the invention is better understood, the invention consists in the novel combination and arrangement of parts hereinafter more fully described, illustrated and claimed with reference being made to the attached drawings.

BRIEF DESCRIPTION OF THE DRAWINGS

FIG. 2 of the present invention is a side view of the present invention partially in section, showing the details of its construction.

FIG. 3 is a front view of the present invention, showing further details.

FIG. 4 is a front view of an alternate embodiment of the present invention, disclosing a larger residue container.

Similar reference characters denote corresponding features consistently throughout the several figures of the attached drawings.

DETAILED DESCRIPTION OF THE PREFERRED EMBODIMENTS

Figure 1:
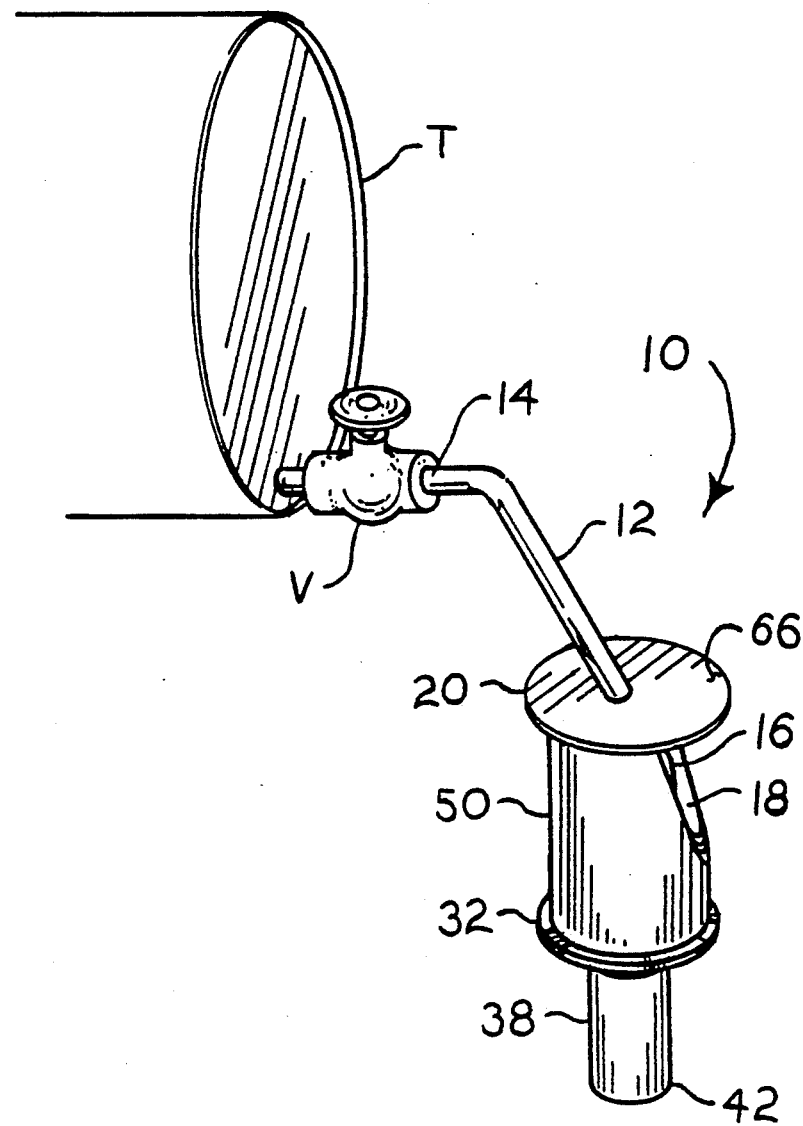
FIG. 1 is a perspective view of the fluid catch collector or container of the present invention in an open position.

Referring now particularly to FIG. 1 of the drawings, the present invention will be seen to relate to a fluid residue catch collector 10 which may be secured to a drain valve V and/or tank T or other fluid container.

Collector 10 includes a drain pipe or tube 12 (either including a bend, as shown in FIG. 1, or straight, as shown in the remaining figures) which has a first or upper end 14 which is threaded or otherwise secured into a valve V or other drain or sampling means. The opposite second or lower end 16 of drain pipe 12 is contained within a first or upper chamber 18, with the roof or upper boundary of the chamber 18 defined by an upper plate 20 which is welded or otherwise secured to pipe 12 immediately above the lower end 16. (Generally, all permanent and fixed joints of collector 10 are welded in order to produce a sealed, leakproof joint. However, other means of assembly may be used as desired and as appropriate for the materials and construction of collector 10.) Pipe 12 may be secured to the upper plate 20 at an acute angle A of other than 90 degrees, as shown in FIG. 2, in order to keep the major axis X of collector 10 vertically aligned. The lower end 16 of drain pipe 12 is preferably formed with a beveled opening 22 which may be parallel to the vertical axis X of collector 10, to provide for easier sampling of any fluid output therefrom, as will be explained further below.

The sides of upper chamber 18 are defined by a fixed, generally cylindrical tube or pipe 24 of relatively large outside diameter D1 in comparison with drain pipe 12 (e.g., approximately 2 inches for pipe 24; other sizes may be used as appropriate for the specific usage of a given container 10). The upper edge 26 of the upper chamber tube 24 is welded or otherwise secured to the bottom surface 28 of the upper plate 20. The lower edge 29 of tube 24 is welded or otherwise secured to the upper surface 30 of a lower plate 32 which defines the lower limit of the upper chamber 18.

The lower plate 32 is not a solid disc, but includes an opening 34 therein to allow the upper chamber 18 to communicate with a lower chamber 36. A section of pipe or tube 38 defines the side walls of the lower chamber 36, and includes a bottom plate or cap 40 which is welded or otherwise secured to the lower end 42 of the tube 38. The upper end 44 of tube 38 is threaded or otherwise formed to cooperate with a collar 46, which collar 46 is welded or otherwise secured to the lower surface 48 of the lower plate 32.

Collector 10 will be seen to include a second, outer section of pipe or tube 50 which serves as a closure means for collector 10. Closure tube 50 has an inner diameter D2 (shown in FIG. 2) which is at least slightly larger than the outer diameter D1 of the upper chamber pipe section 24. Closure tube 50 is also slightly shorter than the distance between the upper plate 20 and the lower plate 32, thereby providing a small clearance space thus to define as a 52 between the upper end 54 of closure pipe or tube 50 and the bottom surface 28 of the upper plate 20. The clearance provided by the slightly larger inner diameter D2 of closure pipe 50 and the gap 52 at the top, results in closure tube 50 having a limited amount of play relative to the other fixed components of collector 10 and enabling closure pipe 50 to be rotated freely about the upper chamber pipe 24. The two pipes or tubes 24 and 50 will be seen to be axially concentric relative to one another.

The fixed upper chamber tube or pipe 24 and the rotatable closure pipe 50 are each cut at an angle 56 as shown in the side view of FIG. 2, thereby respectively forming openings 58 and 60 therein with openings 58 and 60 each having conical sections as shown in FIG. 3. The openings 58 and 60 will be seen to extend from a maximum width of slightly less than the respective diameters of tubes 24 and 50, tapering downward to the sides of tubes 24 and 50 above their respective lower ends 29 and 62. As the axially rotatable closure tube or pipe 50 may be freely rotated about the fixed upper chamber pipe 24, it will be seen that the closure pipe opening 60 may be axially displaced relative to the upper chamber tube or pipe opening 58 to effectively and substantially close the upper chamber 18 to the outer environment.

Collector 10 is installed at the output of a drain valve V or other location as desired by threading or otherwise securing the first or upper end 14 of drain pipe 12 into the valve V. Collector 10 is oriented so that the axis X of collector 10 is substantially vertical, thereby to cause any residue or fluid which may issue from the lower or second end 16 of pipe 12 to fall downward and be contained within the lower chamber 36 of collector 10. Collector 10 is used by rotating the axially rotatable closure pipe 50 relative to the fixed upper chamber pipe 24 to align the two openings 58 and 60 with one another and thereby access the opening 22 of pipe 12, as shown in the drawing figures. A collection container may then be placed immediately beneath the angled opening 22 of pipe 12 and the valve V opened to allow fluid to flow therethrough, as indicated by the fluid flow arrow 64 of FIG. 2, and outward through pipe 12 to provide a sample for the collection container. Collector 10 may be used alternatively as a drain means for the pipe, tank or other apparatus to which it may be connected, by operating it in the same manner but connecting another drain pipe or hose to the outlet end 16 of pipe 12.

When the sampling or draining of fluid is completed, the valve V is closed and the axially rotatable closure pipe 50 is rotated about the concentric fixed upper chamber pipe 24 to place the closure pipe opening 60 diametrically opposite the upper chamber pipe opening 58. The effective closure of the opening 58 of the fixed pipe or tube 24 by covering that opening 58 with the wall of the rotatable pipe 50, serves to prevent any fluid residue which may continue to run downward from the valve V by means of pipe 12, from being wind blown outward to contaminate the environment. Such fluid residue will drip or run downward into the upper chamber 18 of collector 10, continuing downward to collect within the lower chamber 36. The substantially enclosed volume of the upper and lower chambers 18 and 36 further serve to preclude the entry of liquids from precipitation, wash water runoff, etc. into those chambers, thereby preventing the washing of any residue fluids therefrom by filling the chambers 18 and 36 with precipitation or runoff. The relatively wide upper plate 20 and overhanging flange 66 serve to prevent water or other fluids from running downward from the top of collector 10 and thence downward between the two pipes or tubes 24 and 50 to fill or flood the chambers 18 and 36 and washing out any residue which may be contained therein. Another advantage provided by the present invention is the prevention of windblown or other contamination from entering the end of the pipe 12 and contaminating the sample.

From time to time as needed, the lower chamber 36 may be removed from the remainder of collector 10 in order to dispose of any residue which may have collected therein. Once such residue has been disposed of, the lower chamber may be reinstalled to collector 10 by threading or otherwise securing the lower chamber pipe or side wall means 38 to the collar 46.

An alternative embodiment to the above collector 10 is shown in FIG. 4. Collector 10a of FIG. 4 includes components 12a through 34a and 44a through 66a, which are respectively identical to like numbered components 12 through 34 and 44 through 66 of collector 10 of FIGS. 1 through 3. However, the lower chamber 36 and its respective components of collector 10 have been replaced by a larger collection apparatus in the case of collector 10a. Collector 10a includes a lower chamber 68 defined by a tube or pipe section 70 tapering in a funnel shape to a smaller bottom outlet portion 72. The tube or pipe 70 defining the lower chamber 68 of collector 10a will be seen to secure to collar 46a and communicate with the upper chamber 18a, in the same manner as the lower chamber 36 of collector 10. However, the bottom outlet 72 includes an opening 74, thus allowing any residue fluid escaping from the lower end of pipe 12a to pass through the upper chamber 18a, lower chamber 68, and thence outward through opening 72.

In order to contain any such fluid, a remote reservoir 76 is provided which is connected to and communicates with the bottom outlet 72 of collector 10a by means of a hose, tube or pipe 78. Remote reservoir 76 includes a top or lid 80 to prevent the entrance of other contaminants into the interior thereof, side walls 82, and a bottom 84 sealed to the side walls 82 to prevent leakage of fluid therefrom. By positioning the remote reservoir 76 below the outlet 72 of the lower chamber 68 of collector 10a, any fluid residue arriving in lower chamber 68 will continue downward through the outlet opening 74 and hose 78 and into the remote reservoir 76. By providing such a remote reservoir 76, a much larger volume for the containment of fluid residue may be provided than is the case with the lower chamber 36 of collector 10, thus allowing greater amounts of fluid residue to be collected and/or longer periods of time to pass before emptying the reservoir is necessary.

The operation of collector 10a will be seen to be identical to that of collector 10, with the exception of the remote reservoir 76 and its connection with the remainder of collector 10a. The axially concentric pipes or sleeves 24a and 50a and their truncated openings provide for the opening or closure of the upper chamber 18a by means of the rotational displacement of the outer pipe or sleeve 50a, in the manner of pipe or sleeve 50 of collector 10.

The materials from which collectors 10 and 10a may be constructed will vary depending upon the environment in which a collector 10 or 10a is to be used. Preferably, all of the components of collectors 10 and 10a are formed of stainless steel with welded joints, in order to provide resistance from corrosion due to hazardous acids or other chemicals as well as the outdoor environment and weather. However, other materials may be used as desired and/or required, such as aluminum, plastics of various types, etc. In any case, collectors 10 and 10a will be seen to provide an environmentally secure containment apparatus for any fluid residue which may seep or escape from an outlet or collection point valve, while still allowing sampling or other access activity to take place with ease by merely rotating the outer sleeve to align the two openings of the inner and outer sleeve. The apparatus precludes any ingress of other agents or egress of fluid residue, yet allows the environmental pressure to communicate with the upper and lower chambers of the collector by means of the gap at the upper end of the outer sleeve. Accordingly, no differential pressure will build up within the apparatus, obviating any requirement for pressure vessels and their associated expense.

It is to be understood that the present invention is not limited to the sole embodiments described above, but encompasses any and all embodiments within the scope of the following claims.

I claim:

1. A collector providing for the sampling, drainage, collection and containment of fluid residue escaping from an outlet valve, comprising:
    an upper chamber having a volume therein and defined by an upper plate, side walls and a lower plate, with said side walls having a first opening means therethrough and said lower plate having a second opening means therein;
    a drain pipe, having a first end and a second end;
    said upper chamber communicating with the outlet valve by means of said drain pipe, with said drain pipe first end connected to the outlet valve and said second end passing through said upper plate and opening into said second chamber;
    a lower chamber having a volume therein and defined by said lower plate, side walls and a bottom;
    said lower chamber communicating with said upper chamber by said second opening means in said lower plate; and
    an axially concentric and rotatable outer closure sleeve including third opening means therein and surrounding said upper chamber, whereby;
    said outer closure sleeve is axially rotated about said upper chamber of said collector to align said third opening means of said outer closure sleeve and said first opening means of said side walls of said upper chamber, the outlet valve is opened, and fluid is drained from said second end opening of said drain pipe and accessed by means of said aligned first and third opening means, with any fluid residue remaining after the outlet valve is closed being collected within said collector and protected from the elements by axially rotating said outer closure sleeve to displace said outer closure sleeve third means from said side walls first opening means.

2. The collector of claim 1 wherein:
said lower chamber includes a sealed bottom, whereby fluid residue is contained within said lower chamber.

3. The collector of claim 1 wherein:
said lower chamber includes a bottom outlet having fourth opening means therein;
a remote reservoir including a top, side walls, and a bottom; and
passage means extending between said lower chamber bottom outlet and said remote reservoir, for communicating said remote reservoir with said lower chamber.

4. The collector of claim 1 wherein:
said lower chamber is removable.

5. The collector of claim 1 including:
Collar means affixed immediately below said lower plate and providing for the removable attachment of said lower chamber.

6. The collector of claim 1 wherein:
said side walls of said upper chamber and said outer closure sleeve are each generally cylindrical, with said upper chamber side walls having an outside diameter and said outer closure sleeve having an inside diameter; and
said upper chamber outer side walls outside diameter being less than said outer closure sleeve inside diameter, whereby said outer closure sleeve is freely rotatable about said upper chamber side walls.

7. The collector of claim 1 wherein:
said upper plate includes a lower surface;
said outer closure sleeve includes an upper edge spaced apart from said upper plate lower surface and defining gap means therebetween; whereby
vertical play is provided for said outer closure sleeve about said upper chamber side walls, thereby permitting free rotational movement of said outer closure sleeve about said upper chamber side walls and further allowing said volume of said upper chamber and said lower chamber to communicate with the external environment to preclude requirement for pressure sealing means.

8. The collector of claim 1 wherein:
said side walls of said upper chamber comprise a generally cylindrical sleeve and said side walls first opening means comprises an angled cut forming a first open conical section in said cylindrical sleeve.

9. The collector of claim 1 wherein:
said outer closure sleeve is generally cylindrical and said outer closure sleeve third opening means comprises an angled cut forming a second open conical section in said outer closure sleeve.

10. The collector of claim 1 wherein:
said upper plate includes an overhanging flange extending outward past said outer closure sleeve, whereby;
extraneous contaminants are precluded from entering said upper chamber by flowing downward between said upper chamber side walls and said outer closure sleeve.

11. The collector of claim 1 wherein:
said upper chamber and said lower chamber each include a vertically aligned axis; and
said drain pipe forms an acute attachment angle with said upper plate relative to said vertically aligned axis, with said drain pipe opening formed in a plane parallel to said vertically aligned axis and aligned with said upper chamber side wall opening.

12. The collector of claim 1 wherein:
said collector is formed of stainless steel.

13. The collector of claim 1 wherein:
said collector is formed of aluminum.

14. The collector of claim 1 wherein:
said collector is formed of plastic.

* * * * *